US007317954B2

(12) United States Patent
McGreevy

(10) Patent No.: US 7,317,954 B2
(45) Date of Patent: Jan. 8, 2008

(54) VIRTUAL CONTROL OF ELECTROSURGICAL GENERATOR FUNCTIONS

(75) Inventor: Francis T. McGreevy, Aurora, CO (US)

(73) Assignee: ConMed Corporation, Utica, NY (US)

( * ) Notice: Subject to any disclaimer, the term of this patent is extended or adjusted under 35 U.S.C. 154(b) by 470 days.

(21) Appl. No.: 10/735,475

(22) Filed: Dec. 12, 2003

(65) Prior Publication Data

US 2005/0128183 A1  Jun. 16, 2005

(51) Int. Cl.
| A61B 1/00 | (2006.01) |
| A61B 18/04 | (2006.01) |
| A61B 18/18 | (2006.01) |
| A61N 1/00 | (2006.01) |
| G05B 15/00 | (2006.01) |

(52) U.S. Cl. .............................. 700/83; 378/8; 378/168; 378/179; 600/101; 600/118; 382/103; 607/115; 607/119; 607/122; 606/34; 606/41; 606/35

(58) Field of Classification Search .................. 700/83; 378/8; 345/168; 606/34–50; 361/681; 600/101, 437; 607/115–123
See application file for complete search history.

(56) References Cited

U.S. PATENT DOCUMENTS

| 4,148,019 A | * | 4/1979 | Durkee ........................ 340/531 |
| 4,867,551 A | * | 9/1989 | Perera ......................... 351/158 |
| 5,370,645 A | * | 12/1994 | Klicek et al. .................. 606/35 |
| 5,678,568 A | | 10/1997 | Uchikubo et al. |
| 5,688,269 A | * | 11/1997 | Newton et al. ................ 606/46 |
| 6,040,811 A | * | 3/2000 | Malhi .......................... 345/87 |
| 6,063,030 A | * | 5/2000 | Vara et al. ................... 600/437 |
| 6,175,610 B1 | * | 1/2001 | Peter .............................. 378/8 |
| 6,231,569 B1 | * | 5/2001 | Bek et al. ...................... 606/34 |
| 6,266,048 B1 | * | 7/2001 | Carau, Sr. ................... 345/168 |
| 6,286,512 B1 | * | 9/2001 | Loeb et al. .................. 128/898 |
| 6,323,942 B1 | | 11/2001 | Bamji |

(Continued)

FOREIGN PATENT DOCUMENTS

DE  19714984 A1  11/1997

(Continued)

OTHER PUBLICATIONS

Paul F. Laeseke et al., Postbiopsy Bleeding in a Porcine Model: Reduction with Radio-Frequency Ablation—Preliminary Results, RSNA, May 2003.*

(Continued)

Primary Examiner—Anthony Knight
Assistant Examiner—Sunray Chang
(74) Attorney, Agent, or Firm—John R. Ley

(57) ABSTRACT

A virtual control panel controls the functionality of an electrosurgical generator in response to interrogating, preferably optically, an object, such as a user's finger, interacting with a control panel image as an act of control input over the functionality of the generator. The control panel image is presented, preferably by optical projection, on a display surface of a display surface structure. The control panel image may include, in addition to a contact control area where interaction with the object is interrogated, a display area where information describing the functionality of the generator is presented, preferably by optical projection. A virtual pad can be used with the virtual control panel to divide and separate control and display functionality.

60 Claims, 9 Drawing Sheets

U.S. PATENT DOCUMENTS

| | | | |
|---|---|---|---|
| 6,377,238 B1 | 4/2002 | McPheters | |
| 6,402,741 B1 * | 6/2002 | Keppel et al. | 606/34 |
| 6,512,838 B1 | 1/2003 | Rafii et al. | |
| 6,515,740 B2 | 2/2003 | Bamji et al. | |
| 6,522,395 B1 | 2/2003 | Bamji et al. | |
| 6,580,496 B2 | 6/2003 | Bamji et al. | |
| 6,587,186 B2 | 7/2003 | Bamji et al. | |
| 6,633,658 B1 * | 10/2003 | Dabney et al. | 382/128 |
| 6,652,514 B2 * | 11/2003 | Ellman et al. | 606/37 |
| 6,710,770 B2 * | 3/2004 | Tomasi et al. | 345/168 |
| 7,052,494 B2 * | 5/2006 | Goble et al. | 606/45 |
| 7,226,447 B2 * | 6/2007 | Uchida et al. | 606/34 |

FOREIGN PATENT DOCUMENTS

| | | |
|---|---|---|
| DE | 19805529 A1 | 2/1998 |
| DE | 200010134 U1 | 1/2000 |

OTHER PUBLICATIONS

Holograp Controls, Keep Operating Rooms Clean and Uncluttered; Medical Design News, May/Jun. 2003; pp. 10 and 12.

Type It Anywhere, Mike May, Scientific American, Jan. 2003, pp. 32 and 33.

International Application Publication No. WO 02/100285 A1; International Application No. PCT/SG01/00119; dated Dec. 19, 2002.

PCT International Search Report for International Application No. PCT/US2004/041336, dated Apr. 15, 2005.

PCT International Search Report, dated Apr. 12, 2005.

Written Opinion of the International Searching Authority, dated Apr. 12, 2005.

* cited by examiner

VIRTUAL CONTROL OF ELECTROSURGICAL GENERATOR FUNCTIONS

CROSS-REFERENCE TO RELATED APPLICATION

This invention is related to another invention made by the present inventor for Virtual Operating Room Integration described in U.S. patent application Ser. No. (24.352), filed concurrently herewith. The subject matter of this concurrently filed application is incorporated herein by this reference.

FIELD OF THE INVENTION

This invention relates to electrosurgical generators, and more particularly to a new and improved virtual control panel for an electrosurgical generator which optically displays a control panel image and which interrogates interaction with a control panel image to control the functionality of the electrosurgical generator. Among other things, the virtual control panel permits a surgeon to directly control the electrosurgical generator from within a sterile field at an operating site, and permits the functionality of the electrosurgical generator to be adjusted and displayed as desired without reliance on physical components normally fixed in a typical physical control panel of a conventional electrosurgical generator.

BACKGROUND OF THE INVENTION

Electrosurgical generators have various control devices located on a front control panel to permit the user to select different functions of the generator and to select and adjust output power characteristics of the generator. For instance, the mode of operation of the generator is selected by manipulating selector switches or buttons to cut tissue, to coagulate blood flow from the tissue, or to cut and coagulate simultaneously in a monopolar mode of operation. A bipolar mode of operation is used primarily for coagulation of blood flow. In addition, after selecting the mode of operation, the output power characteristics may be selected by manipulating other selected switches or buttons. In some modes of operation, such as simultaneous cutting and coagulation, the characteristics of the output power delivered may further be selected and adjusted from front panel control devices. Other functionality of the generator is also obtained by manipulating other types of front panel control devices.

The front panel control devices of the electrosurgical generator cannot be positioned within the sterile field where the surgeon is operating because it is not possible to disinfect and sterilize the entire electrosurgical generator of which the front panel control devices are a part. Typical front panel control devices are complex structures with movable components and other intricate mechanical and electrical parts. The complex nature of these control devices does not permit disinfectant solutions from penetrating into their inner regions, and thus sterilization cannot be achieved. Moreover, a somewhat intricate and delicate nature of these control devices are not sufficient to withstand high temperature sterilization.

A typical front control panel for electrosurgical generator also has displays for displaying information concerning the functionality of the generator, such as the selected mode of operation and amount of output power delivered. Such displays are also not capable of being sterilized, either by a disinfectant solution or by the application of heat, for the same reasons that the front panel control devices cannot be sterilized.

During the course of a typical surgical procedure, it is necessary to adjust the mode of operation and the output power characteristics of the electrosurgical generator. Some types of surgical procedures require almost constant adjustments. The surgeon performing the procedure determines what adjustments must be made and when to make them. Because the electrosurgical generator, including the front panel controls, cannot be sterilized, the electrosurgical generator must remain outside of the sterile field surrounding the surgical site where the surgeon is performing the procedure. Because adjustments must be made during the course of the procedure, the surgeon must rely on an assistant to make adjustments. The assistant must remain outside of the sterile field, because the assistant is interacting with the non-sterile front control panel of the electrosurgical generator.

The assistant makes adjustments to the front panel control devices in response to verbal commands from the surgeon. Such verbal communication may be prone to misinterpretation, and the changes in operating characteristics of the electrosurgical generator may not be made as quickly as the surgeon may desire, due to the fact that the assistant may not be responsive at the time of the verbal command because of other responsibilities in the operating room. In any event, the necessity to rely on an assistant to control the electrosurgical generator can become a source of distraction or frustration to the surgeon, particularly in intense procedures which require numerous adjustments during the course of the procedure. However, the requirement for a sterile field around the surgical site necessitates such indirect control techniques.

In a similar sense, the surgeon must rely on the assistant to communicate power settings and other information describing the functionality of the generator, because the generator is located outside of the sterile field. While it is possible for the surgeon to divert his or her attention from the surgical site to view the displays of information presented on the front panel of the generator, such movement is a distraction. Moreover, the electrosurgical generator must be placed outside of the sterile field but within eyesight of the surgeon, if the surgeon is to view information displayed on the front panel of the electrosurgical generator. In many circumstances, it is impossible for the electrosurgical generator to be placed so that it could be directly viewed by the surgeon.

The electrosurgical generator is typically located in the operating room close to the operating table since the electrical conductors must extend from the electrosurgical generator to a handpiece held by the surgeon to apply the electrical energy to the patient. The front panel of the electrosurgical generator must be accessible to an assistant so that the surgeon's verbally commanded selections and adjustments can be made. Locating the generator to accommodate these requirements means that the generator is usually positioned on a cart relatively close to the operating table. Positioned in this manner, the electrosurgical generator takes up valuable space around the operating table. A number of people are usually present in the operating room and surround the operating table during the course of the procedure, particularly in complex procedures. The necessity to locate the electrosurgical generator relatively close to the operating table diminishes the amount of space available for surgeons and assistants surrounding the patient and adds to the congestion during the procedure.

One approach to controlling the electrosurgical generator utilizes a holograph to project an image of the controls into empty three-dimensional space within the operating room. When an object enters the three-dimensional space in which the holographic image of the controls is located, an adjustment to the generator is made. Allowing the surgeon to interact with a holographic image allows the surgeon to establish direct control over the surgical equipment without compromising the sterile field. However, holographic images introduce new problems. One such problem stems from the fact that holographic images can only be viewed from a relatively narrow field of vision, which means that the holographic image may not always be seen by the surgeon. For the surgeon to view the holographic controls, the light projection equipment that creates the hologram has to be adjusted in a particular location in the operating room, or the surgeon must shift his or her position at the operating table, or the surgeon must again rely on an assistant to interact with the hologram to achieve control over the surgical equipment. Moreover, because the hologram exists in three-dimensional space, an individual or object can inadvertently move through the three-dimensional space and interact with the hologram in such a way to create an unintended adjustment of or control over the electrosurgical generator. This is especially the case if the hologram is placed near the surgical site where there is much activity during surgery. Furthermore, because the hologram is placed in space away from the surgical site, the surgeon must look up or turn to see and interact with the hologram, which is inconvenient and distracting for the surgeon and can interfere with the surgeon's concentration.

The control and display devices are physically located in fixed positions on the front panel of the electrosurgical generator during its manufacture. The physical position of these control and display cannot thereafter be changed to accommodate any preferences for organization, layout, and presentation. Also, if the functionality of the electrosurgical generator is upgraded, the new functionality must operate with the existing arrangement of front panel control and display devices. Therefore, the fixed configuration of the front panel control and display devices serves as a limitation on the ability of the surgeon or the surgical personnel to organize and control the electrosurgical generator for optimum use and convenience, and also limits the opportunities to upgrade or change the operating characteristics of the electrosurgical generator.

SUMMARY OF THE INVENTION

The present invention provides a virtual control panel with an optical image of contact control areas and display areas. The virtual control panel can be sterilized and therefore placed within the sterile field at the surgical site so that the surgeon can directly interact with the virtual control panel and achieve direct control over the functionality of the electrosurgical generator without the need to depend upon an assistant to make selections and adjustments. Interaction by the surgeon with contact control areas of the optical image is interrogated optically and interpreted as a control input to the electrosurgical generator. Information concerning the functionality of the generator is displayed for direct viewing by the surgeon at the surgical site, without requiring the surgeon to divert his attention away from the surgical site or to rely on an assistant for verbal explanations of the generator functionality. The layout of projected control panel image, including the contact control and display areas, may be adjusted to suit the surgeon's primary needs. The amount of information presented, and the options for control, may be limited to those specifically required or desired according to the preferences of the surgeon or the requirements of the surgical procedure.

These and other improvements are achieved by an electrosurgical generator having a virtual control panel for controlling functionality of the electrosurgical generator. The functionality of the electrosurgical generator is controlled in response to interrogating, preferably optically, an object, such as a user's finger, interacting with a control panel image. The virtual control panel comprises a display surface structure having a display surface upon which the control panel image is located. A sensor interrogates an interaction of the object with the control panel image and supplies an interaction signal indicative of interaction of the object with the control panel image. A generator controller of the electrosurgical generator controls the functionality of the electrosurgical generator in response to the interaction signal. Preferably, a projector optically projects the control panel image on the display surface.

In a related manner, the improvements also pertain to a virtual control panel for controlling functionality of an electrosurgical generator and/or for displaying the functionality of the generator. The virtual control panel includes a display surface structure having a display surface. A control panel image is presented on the display surface. To control generator functionality, a sensor interrogates the interaction of the object with the control panel image and creates an interaction signal indicative of the functionality indicated by the interaction of the object with the control panel image. The interaction signal is applied to a generator controller which responds by controlling the generator functionality. To display generator functionality, a projector optically projects the control panel image on the display surface and includes information describing the functionality of the electrosurgical generator. The information describing the generator functionality is obtained from information signals supplied by the generator controller.

The improvements also involve methodology for controlling the functionality of the electrosurgical generator and displaying information describing the functionality of the generator. A control panel image is presented on a display surface of a display surface structure. The control panel image includes a contact control area which represents a function of the electrosurgical generator. An object interacts with the contact control area as an act of selected functionality to be performed by the electrosurgical generator. The contact control area is optically interrogated for interaction by the object, and the functionality of the generator is controlled in response to the interrogation of the interaction of the object with the contact control area. The control panel image may also include a display area onto which is projected information describing the functionality of the electrosurgical generator. The information describing the generator functionality is projected in response to information signals from the generator controller.

The virtual control panel may be used in combination with a separate virtual pad, and the control functionality and display functionality may be distributed between display surfaces of display surface structures associated with both the virtual control panel and the virtual pad. A plurality of control panel images are presented on the display surfaces of a corresponding plurality of display surface structures. At least one control panel image includes a contact control area which represents a function of the electrosurgical generator. At least one other control panel image includes a display area which presents information describing the functionality of the electrosurgical generator. An object interacts with the one contact control area as an act of selected functionality to be performed by the electrosurgical generator, and that interaction is optically interrogated as a basis for controlling the functionality of the generator. Information describing the functionality of the generator is presented in the display area of the one other control panel image.

Preferably, a wireless optical or radio frequency communication link connects the virtual control panel and the virtual pad to the generator controller, thereby allowing the virtual control panel and the virtual pad to be separated from the electrosurgical generator. The virtual control panel and the virtual pad may be made sterilizable so that they can be positioned within the sterile field at the operating site. However, the control panel images may also be presented on an exterior housing of the electrosurgical generator, thereby replacing the conventional physical-component front control panel of the electrosurgical generator. Components of the virtual control panel and the virtual pad may be made disposable.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

DETAILED DESCRIPTION

Figure 1:
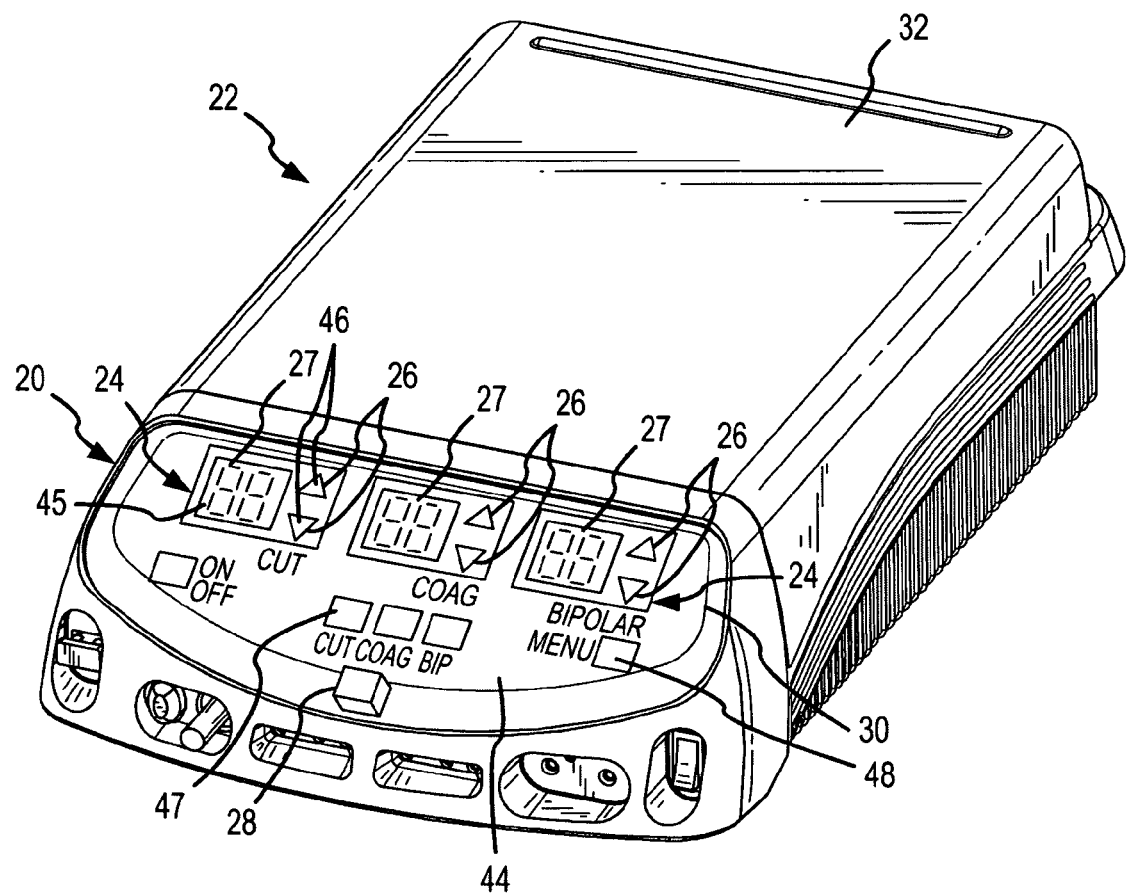
FIG. 1 is a perspective view of an electrosurgical generator and a virtual control panel in which the present invention is embodied.

An exemplary form of a virtual control panel 20 for an electrosurgical generator 22 is shown in FIG. 1. The virtual control panel 20 presents a front control panel image 24 having various contact control areas 26 and display areas 27 created by a projector sensor 28. The projector sensor 28 projects the control panel image 24 including the areas 26 and 27, onto a display surface structure 30. The display surface structure 30 may be either integral with a housing 32 of the electrosurgical generator 22, as shown in FIG. 1, or detachable and removable from the housing 32 as shown in FIG. 4. Physical interaction of an object, such as a finger 34 (FIGS. 3 and 9) of a surgeon 36 (FIG. 9) with the contact control areas 26 of the panel image 24 is interrogated by the projector sensor 28. The physical interaction is interpreted as a control input command to control the functional characteristics the electrosurgical generator 22. For example, direct physical interaction of a surgeon's finger 34 (FIGS. 3 and 9) with a specific contact control area 26 of the control panel image 24 adjusts the output power and/or the output waveform characteristics of the electrosurgical generator 22.

Direct physical interaction with the control panel image 24 controls the functionality of the electrosurgical generator 22 in a manner substantially equivalent to the manner in which the electrosurgical generator 22 is controlled by direct physical contact and manipulation of the conventional physical control panel and display elements (not shown) connected to a conventional electrosurgical generator. However, in the present invention, the contact control areas 26 and display areas 27 of the control panel image 24 replace the conventional physical control panel and display elements of a conventional electrosurgical generator. The use of the virtual control panel 20 with the contact control areas 26 in the display areas 27 eliminate the necessity to use separate physical components for specific control and display purposes in an electrosurgical generator. Moreover, the use of the virtual control panel 20 with the control areas 26 and the display areas 27 avoids the need to permanently incorporate separate physical control and display components in a physical front panel of an electrosurgical generator, but instead provides the opportunity to display only the type of generator controls and information desired.

Figure 2:
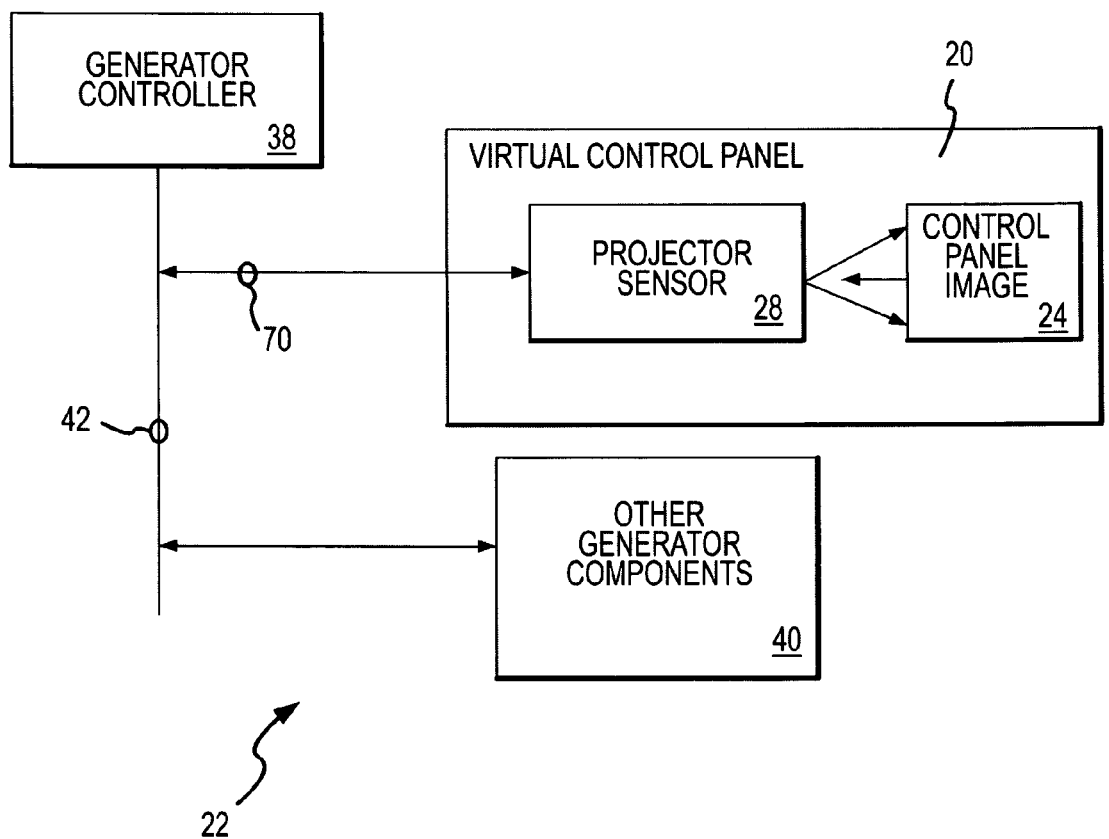
FIG. 2 is a functional block diagram of certain components of the electrosurgical generator and the virtual control panel shown in FIG. 1.

The virtual control panel 20 interacts with a generator controller 38 of the electrosurgical generator 22 as shown in FIG. 2. The generator controller 38 controls the overall functionality and capabilities of the electrosurgical generator 22. An operating program, which is contained in memory (not shown) connected to the controller 38, controls the controller 38 and causes the controller 38 to send control signals to other conventional electrosurgical generator functional components 40 by which to execute the operations necessary to create and achieve electrosurgical functionality, as well as achieve the additional functions and features of the virtual control panel 20.

The virtual control panel 20 and the other generator components 40 are connected to the generator controller 38 by a conventional bus 42. Signal communication on the bus 42 between the generator controller 38 and virtual control panel 20 is two-way or bidirectional, meaning that the information flows in both directions between those components. The generator controller 38 generates and supplies signals to the virtual control panel 20 over the bus 42. The projector sensor 28 projects the control panel image 24 in response to the signals supplied by the generator controller 38 and from programmed information within the projector sensor 28 itself. The projector sensor 28 interrogates the interaction of the surgeon's finger 34 (FIGS. 3 and 9) with the contact control areas 26 of the control panel image 24, and supplies an interaction signal to the generator controller 38 which represents the fact, type and degree of this interaction.

The generator controller 38 interprets the interaction signal as a control input to the electrosurgical generator 22 and supplies control signals over the bus 42 to the other functional components 40 to control functionality of the electrosurgical generator 22. The functional components 40 respond to the control signals from the controller 38 and create corresponding functionality and adjustments in the functionality of the electrosurgical generator 22. The other generator components 40 may supply information to the controller 38 such as, for example, the power level settings of an electrosurgical generator. The information from the functional components 40 is sent from the controller 38 to the projector sensor 28. The projector sensor 28 presents the information in the display area 27 of the control panel image 24. For example, the display area 27 of the control panel image 24 may display the power level setting of the electrosurgical generator 22. In this manner, the generator controller 38 transmits and receives control, status, functionality and condition information over the bus 42, thereby establishing the control and flow of information within the electrosurgical generator 22 to and from the other generator components 40 and the virtual control panel 20.

The projector sensor 28 projects the control panel image 24 onto a relatively flat display surface 44 of the display surface structure 30. The display surface structure 30 may form a portion of the electrosurgical generator housing 32, as shown in FIG. 1, or the display surface structure 30 may be removable from the generator housing 32 as shown in FIG. 4. In either case, the projector sensor 28 is connected or positioned to project the control panel image 24 onto the adjacent display surface 44 and to interrogate the interaction of an object, such as the surgeon's finger 34 (FIGS. 2 and 9), with the contact control area 26 of the image 24. The display surface 44 is preferably textured and colored to provide adequate contrast with the control panel image 24 for easy viewing. The display surface 44 can have a matte finish and can be colored white, or can have another suitable colors and/or textures as needed or desired.

Exemplary contact control areas 26 and display areas 27 of the control panel image 24 are shown in FIGS. 1 and 4. The control panel image 24 includes the display area 27 where information concerning the electrosurgical generator 22 is displayed, such as the amount of output power delivered, as shown at a display portion 45. One contact control area 26 permits increasing and decreasing the quantity displayed at 45, as shown at a contact control portion 46. A further contact control portion 47 of the contact control area 26 permits selection of the generator functionality, such as for the conventional cutting, coagulation, blend (combined cutting and coagulation) and bipolar modes of the electrosurgical operation. Another contact control portion 48 of the contact control area 26 presents a menu selection function, where values and operations may be selected. Upon selecting one of the menu options by contacting the menu contact control portion 48, the entire control panel image 24 on the display surface structure 30 may be changed to present information display and control options selected from the menu.

In this regard, the virtual control panel 20 offers significant advantages over a conventional control panel for electrosurgical generator in that the control panel image 24 can be changed or modified, unlike a conventional control panel which cannot be changed because of its physically fixed configuration. The virtual control panel 20 therefore offers the improvement of presenting information in differing formats and layouts according to the preference of the user. Moreover, the contact control capability and information display capability of the electrosurgical generator can be changed by changing the control panel image 24, to accommodate upgrades and changes to the electrosurgical generator 22. Such changes may not be accommodated in conventional electrosurgical generators due to the fixed structure and components employed in the front panel of the conventional electrosurgical generator. The virtual control panel 20 permits the user to select the information to be displayed in the display areas 27, and permits the user to select and present the relevant control functions in the contact control areas 26, among other important improvements.

Figure 3:
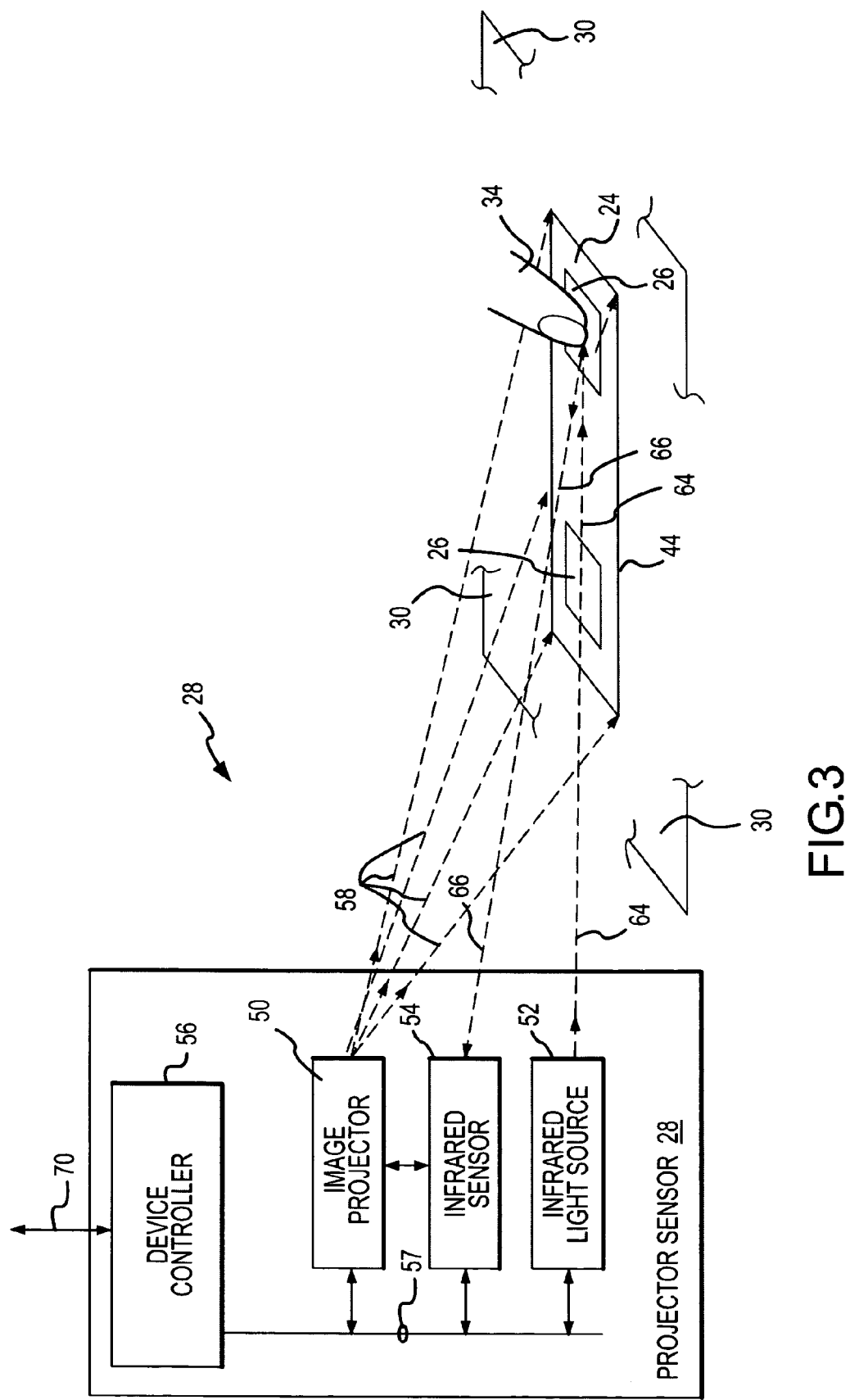
FIG. 3 is a functional block diagram of components of virtual control panel shown in FIGS. 1 and 2.
Figure 4:
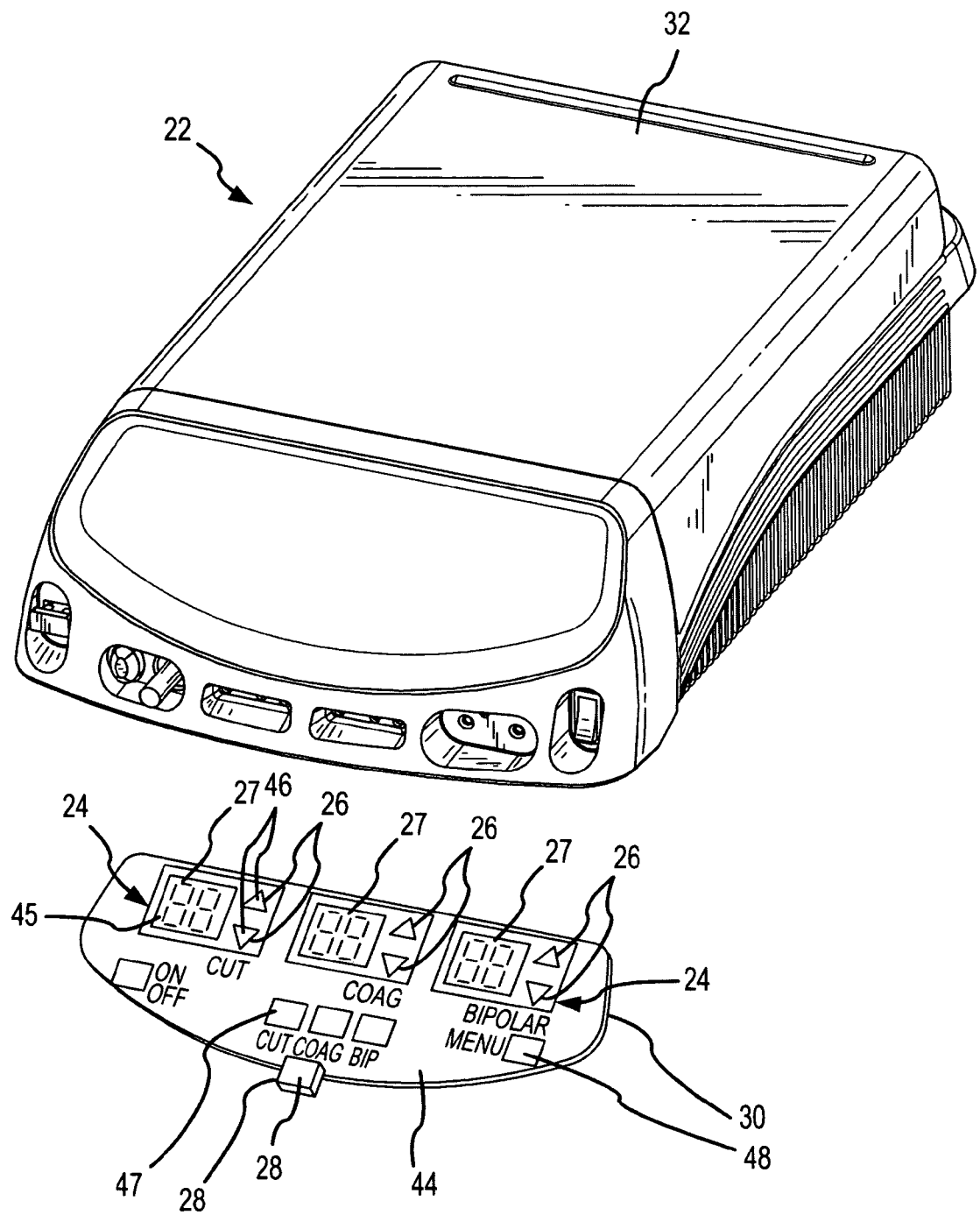
FIG. 4 is a perspective view of an electrosurgical generator similar to the one shown in FIG. 1, illustrating a detachable front panel with which the virtual control panel is used.

More details concerning the functionality of the virtual control panel 20 are shown in FIG. 3. The virtual control panel 20 uses similar components and functions similarly to a virtual keyboard device manufactured by Canesta of San Jose, Calif.

The projector sensor 28 of the virtual control panel 20 includes an image projector 50, an infrared light source 52, an infrared sensor 54, and a device controller 56. The device controller 56 is preferably microprocessor based and functions as a computer with memory to control the image projector 50, the infrared light source 52 and infrared sensor 54 by communicating signals over a bus 57. The image projector 50 projects a light beam 58 onto the display surface 44 of the display surface structure 30 (FIGS. 1 and 4) to scan and create the geometric pattern and designations of the contact control areas 26 and the display areas 27 of the control panel image 24. Scanning of the light beam 58 over the display surface 44 occurs rapidly, causing the image 24 to appear whole to the viewer, even though only a small portion of the image 24 is actually illuminated by the light beam 58 at each instant of time. The scanning angle of the light beam 58 relative to the surface 30 is sufficient to avoid an object, such as the surgeon's finger 34, blocking the light beam 58 from the image projector 50 until that object comes relatively close to touching the display surface 44 upon which the image 24 is projected.

Control information supplied from the device controller 56 to the image projector 50 establishes the scanning pattern of the light beam 58 and hence the geometric pattern of the projected image 24. Control signals from the generator controller 38 (FIG. 2) are delivered to the device controller 56 to establish the geometric pattern characteristics of the projected image 24, or alternatively, the memory of the device controller 56 may be programmed to define a desired type of projected image 24.

An infrared light beam 64 is transmitted from the infrared light source 52 onto the projected image 24. The scanning angle of the infrared light beam 64 relative to the display surface 44 is shallower than the scanning angle of the light beam 58 which creates the image 24. The device controller 56 also controls the infrared light source 52 to scan the projected image 24 with the light beam 64. Preferably, the transmitted light beam 64 is synchronized or coordinated with the geometric pattern of the projected image 24, causing the light beam 64 to sweep or scan the same portion of the projected image 24 that is being simultaneously created by the light beam 58 from the image projector 50. When an interactive object, such as the surgeon's finger 34, closely approaches a contact control area 26 of the projected image 24, light from the transmitted beam 64 is reflected from the object as a reflected infrared light beam 66. The infrared sensor 54 receives the reflected light beam 66, and signals the device controller 56 of the receipt of the reflected light beam 66.

The infrared light beam 64 transmitted from the infrared light source 52 is a series of pulses of infrared light. The reflected light beam 66 is also a series of pulses of infrared light, because the reflected light beam 66 is created by the transmitted light beam 64. The time between the delivery of the pulses of the transmitted infrared light beam 64 and the receipt of the corresponding pulses of the reflected infrared light beam 66 is calculated by the device controller 56. This relative timing information establishes the distance of the object in contact with the contact control area 48 from the infrared light source 52 and the infrared sensor 54, in a manner similar to the manner that radar establishes the distance to an object. The horizontal position of the object, e.g. finger 34, interacting with image 24 is established by the horizontal plane scanning angle of the transmitted light beam 64 which caused the light beam 64 to be reflected. The horizontal plane scanning angle of the light beam 64 is synchronized or coordinated with the creation of the image 24 by the projected beam 58.

By using the distance to the object, e.g. finger 34, established by the relative timing information between the corresponding pulses of the transmitted and received light beams 64 and 66, and by using the horizontal scanning angle of the beam 64 which caused the reflection beam 66, both of which are determined and controlled by the device controller 56, the point of interaction of the object 34 with the geometric pattern of the image 24 is established or interrogated. The ability to discriminate interaction of the object 34 with the different contact control areas 26 is thereby obtained. Differentiating between different contact control areas 26 on the projected image 24 assures that the different control functions represented by different contact control areas 26 on the projected image 24 may be separately and individually invoked by bringing the object, such as the surgeon's finger 34, into contact with those areas 26.

A similar technique of determining the point of interaction of the object with the image 24 could be obtained by using two differently-positioned infrared light sources and sensors (not shown) which are similar to the infrared light source 52 and sensor 54. Each of the two light sources 52 and sensors 54 would determine the distance of the object from it. The two different distances would then be used in a triangulation calculation to determine the position of interaction of the object within the image 24 and to thereby interrogate or discriminate the interaction of the object with each portion of the different contact control areas 26.

Because of the relatively shallow angles of the transmitted and reflected infrared light beams 64 and 66 relative to the surface of the display area 30, it is possible to determine when the tip of the object 34 touches the display surface 44. The shallow angles of the light beams 64 and 66 are not blocked until the object touches the display surface 44 or comes relatively close to touching the display surface 44. The device controller 56 interprets the light beams 64 and 66 as indicative of contact with the image 24, and thereby formulates the interaction signal. The interaction signal is communicated from the device controller 56 to the generator controller 38 over the bus 42 (FIG. 2). The generator controller 38 responds to the interaction signal by delivering control signals over the bus 42 to the other generator components 40 (FIG. 2). In this manner, actual contact of the object 34 with the contact control areas 26 of the projected image 24 is interrogated and used as a control input interaction to establish control over the electrosurgical generator 22.

The projected image 24 can be supplemented or replaced by using a print or an overlay (neither shown) which is placed on top of the display surface 44 of the display surface structure 30. The overlay, which is sterile and disposable, has patterns that correspond to contact control areas 26 and open spaces for the display areas 27. The patterned contact control areas 26 are interrogated in the same manner as previously described to determine interaction by the object, e.g. finger 34. Information is displayed in the open display areas in the same manner as previously described. Attaching the overlay to a display area 30 can eliminate the need for the image projector 50, but a projector 50 could also be used in conjunction with an overlay, if desired, to create separate portions of the entire control panel image 24. If both an overlay (not shown) and projector 50 are used, the projector 50 can be used to create those projected portions of the control panel image 24 that change while the overlay presents the non-changing portions of the control panel image 24.

In the embodiment shown in FIG. 1, the projector sensor 28 is attached to the electrosurgical generator housing 44, which allows a direct electrical connection between the virtual control panel 20 and the bus 42 through a conventional direct electrical connection 70 (FIG. 2), such as by wiring or cabling. The virtual control panel 20 can also be made detachable from the electrosurgical generator housing 32, as shown in FIG. 4.

In the detachable virtual control panel 20 shown in FIG. 4, the projector sensor 28 is attached to the display surface structure 30, and the display surface structure 30 is connectable to and detachable from the generator housing 32. The projector sensor 28 is attached adjacent to the display surface 44 so that the control panel image 24 can be projected upon the display surface 44. The display surface structure 30 is preferably made from a conventional material that can be sterilized. The projector sensor 28 is removable from the display surface structure 30 to permit the structure 30 to be sterilized. Alternatively, the projector sensor 28 may be constructed with an exterior housing or enclosure that is hermetically sealed so that the projector sensor 28 can also be sterilized. To accommodate sterilization by heat treatment, the functioning electronics components within the projector sensor 28 are preferably located within the center of the housing or structure of the projector sensor 28, so that the heat applied to the exterior surface is sufficient to sterilize the exterior surface without internal penetration to such an extent that the interior electronic components are damaged. A portion of the hermetically sealed housing for the projector sensor 28 is transparent to light so that the light beams 58, 64 and 66 (FIG. 3) can pass into and out of the projector sensor. As a further alternative, the projector sensor 28 may be made disposable so that it is initially in a sterilized state ready for use at the surgical site 74 (FIG. 9) when removed from a conventional sterilized sealed pouch.

Making the projector sensor 28 and the display surface structure 30 from materials which permit sterilization allows the detachable virtual control panel 30 to be placed within the sterile field surrounding a surgical site 74 (FIG. 9), without introducing pathogens into the sterile field. Placing the sterilized virtual control panel 20 adjacent to the surgical site 74 permits the surgeon to interact directly with the contact control areas 26 of the control panel image 24, and thereby directly control the functionality of the electrosurgical generator 22. Such direct interaction avoids the inconvenience of indirect control in requiring an assistant to make the changes and the potential problems of miscommunication associated with the surgeon verbally ordering the assistant to make the changes. Instead, the surgeon can directly control the electrosurgical generator 22 from within the sterile field of the surgical site 74.

Figure 5:
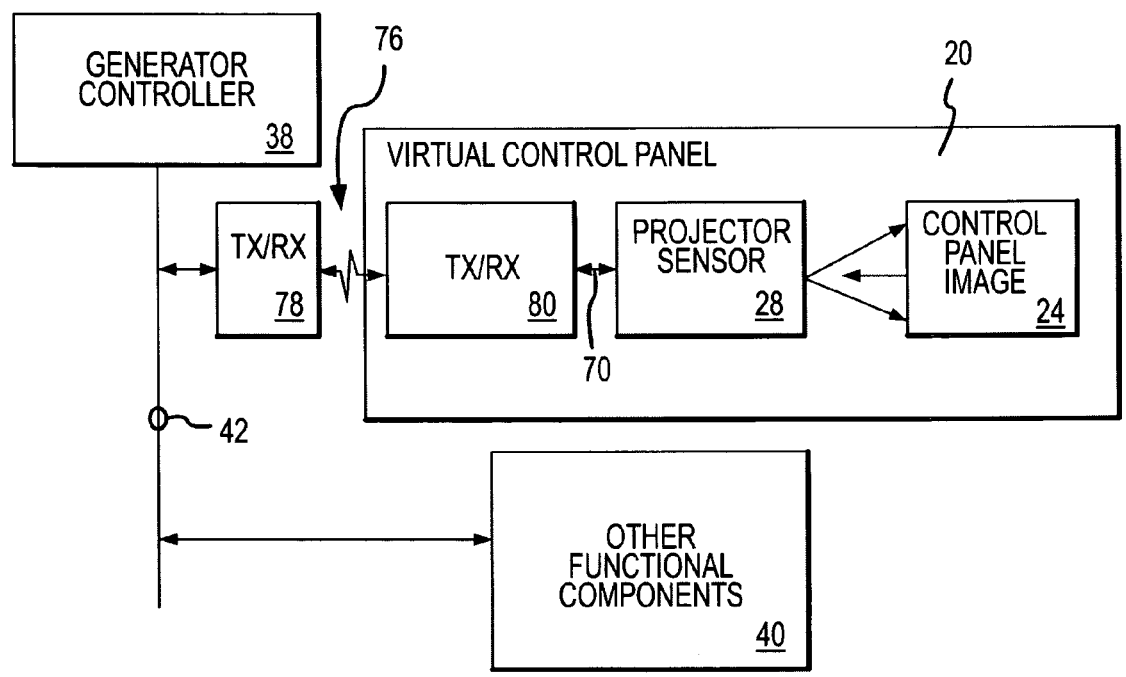
FIG. 5 is a functional block diagram of certain components of the electrosurgical generator and the virtual control panel shown in FIG. 4.

Preferably the detachable virtual control panel 20 communicates with the generator controller 38 through a bidirectional wireless communication link 76 shown in FIG. 5. To establish the bidirectional wireless communication link 76 between the generator controller 38 and the virtual control panel 20, a conventional transceiver 78 is connected to the bus 42 and a corresponding transceiver 80 is connected to the virtual control panel 20. Each transceiver 78 and 80 contains a radio frequency or optical transmitter (Tx) and receiver (Rx), thus making each transceiver 78 and 80 capable of transmitting and receiving information. The transceivers 78 and 80 communicate with each other by transmitting optical or radio frequency signals to establish the wireless communication link 76 as a part of the communication path between the generator controller 38 and the virtual control panel 20. In this manner, control, status, functionality and condition information is transferred between the generator controller 38 and the virtual control panel 20 without requiring an electrical cable 70 (FIG. 2) to connect the generator controller 38 to the virtual control panel 20. The transceiver 80 is connected to the projector sensor 28 and is preferably also contained within the hermetic sealed housing of the sterilizable projector sensor 28. Although not shown, a battery or other type of self-contained power supply may also be contained within the hermetically sealed housing of the projector sensor 28 in order to provide power to the components of the projector sensor 28 to function as described.

The wireless communication link 76 could be replaced with a relatively lengthy electrical cable (not shown) extending between the detachable virtual control panel 20 and the remaining portions of the electrosurgical generator 22. In such circumstances if it is desired to place the detachable virtual control panel 20 within the sterile field of the surgical site 74, such an electrical cable must also be capable of sterilization. In general, if the surgeon is to directly interact with the detachable virtual control panel, the detachable virtual control panel 20 must be sterilized. In any event, the detachable virtual control panel 20 offers the capability of sterilization which was not possible with conventional control panels for electrosurgical generators because the mechanical nature of the control devices that are part of the conventional control panel are incapable of sterilization. The entire virtual control panel 20, including the projector sensor 28 and the display surface structure 30, may be initially supplied in a sterilized state ready for use in the sterile field at the surgical site 74 (FIG. 9) when removed from a conventional sterilized sealed pouch. Similarly, the entire virtual control panel may be made disposable or, alternatively, the display surface structure may be made disposable while the projector sensor 28 is reusable as a result of its capability for sterilization.

In addition to the virtual control panel 20 (FIGS. 1 and 4), a virtual pad 82 may also be used with the electrosurgical generator 22, as shown in FIGS. 6-9. The virtual pad 82 may be used as a substitute for, or an adjunct to, a virtual control panel 20 that is integral to the electrosurgical generator 22 (FIG. 1) or a virtual control panel 20 that is detachable from the housing 32 of the electrosurgical generator 22 (FIG. 4). The virtual pad 82 is another type of a virtual control panel 20, except that the virtual pad 82 will not typically function as the main control panel for the electrosurgical generator. However, the virtual pad 82 can function as the control panel for the electrosurgical generator under circumstances where limited functionality may be required, for example. The virtual pad 82 is a more compact version of the virtual control panel 20, and as such offers a smaller display surface area 44a upon which to project contact control areas 26a and display areas 27a.

Figure 6:
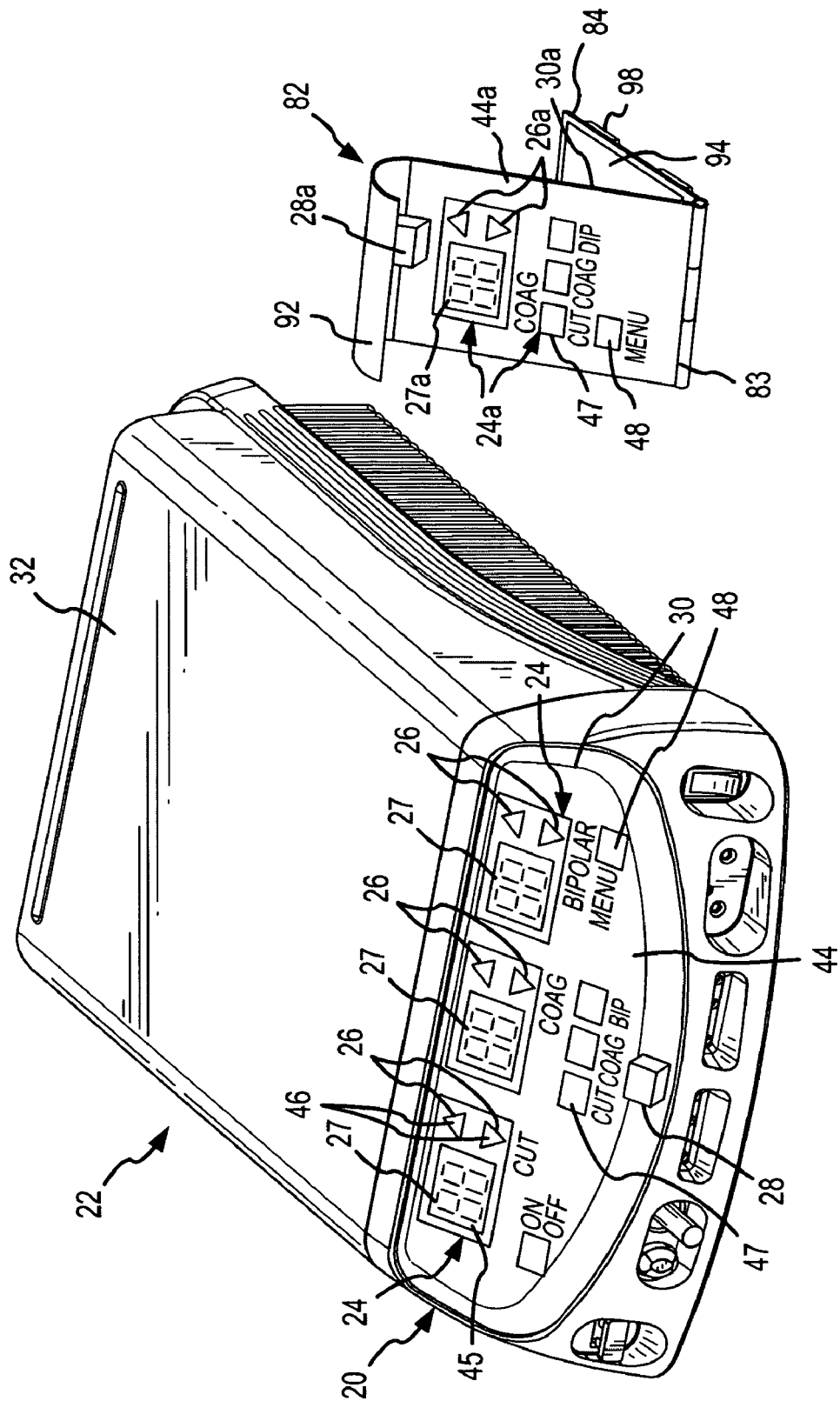
FIG. 6 is a perspective view of an electrosurgical generator and a virtual control panel such as that shown in FIGS. 1 and 4, including an additional virtual pad.
Figure 8:
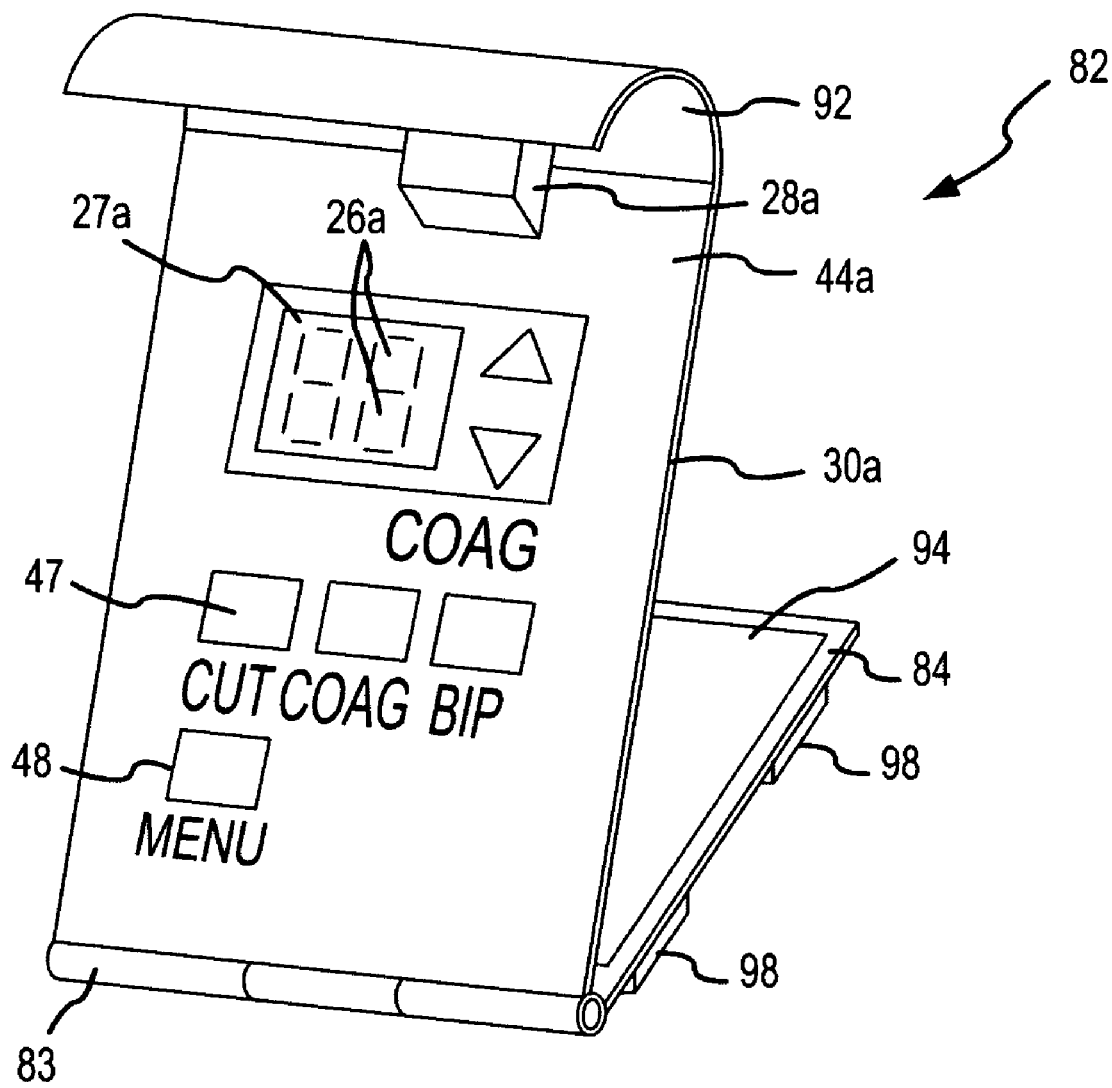
FIG. 8 is an enlarged perspective view of the virtual pad shown in FIG. 6.

Like the virtual control panel 20, the virtual pad 82 includes a projector sensor 28a which is attached to or positioned adjacent to the display surface 44a of a display surface structure 30a, as shown in FIGS. 6 and 8. The projector sensor 28a projects a control panel image 24a having the contact control areas 26a and display areas 27a on the display surface 44a of the display surface structure 30a. The projector sensor 28a is essentially the same as the projector sensor 28 used with the detachable virtual control panel 20 shown in FIG. 4. The interaction of an object such as the surgeon's finger 34 (FIG. 3) with the contact control areas 26a is interrogated by the projector sensor 28a and is interpreted as a control input to the electrosurgical generator 22, in the same manner as previously described in conjunction with FIG. 3.

Figure 7:
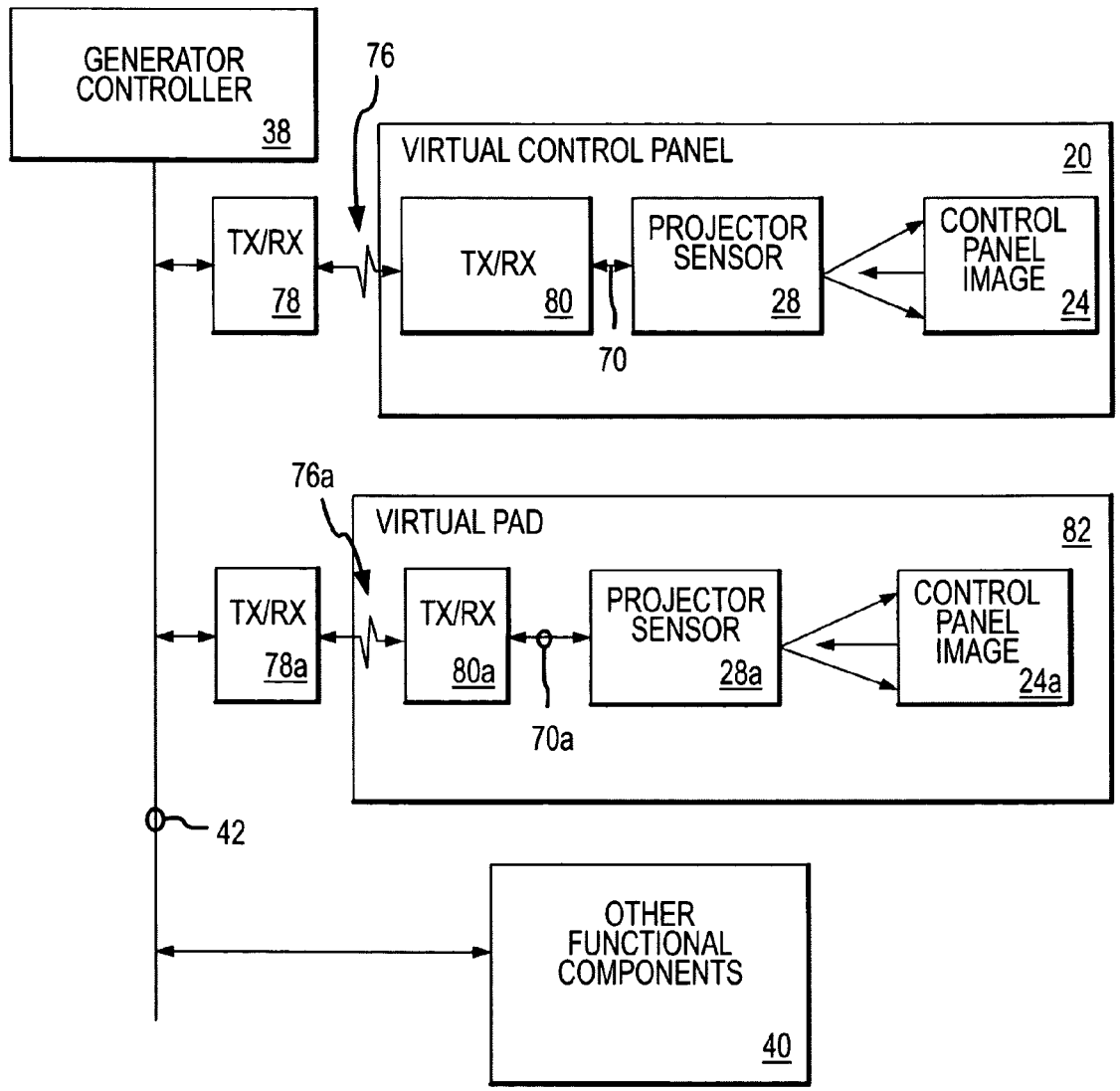
FIG. 7 is a functional block diagram of certain components of the electrosurgical generator, virtual control panel and virtual pad shown in FIG. 6.

The virtual pad 82 also includes a wireless communication link 76a from the projector sensor 28a to the generator controller 38 as shown in FIG. 7. Like the wireless communication link 76 shown in FIG. 5, the wireless communication link 76a to the virtual pad 82 shown in FIG. 7 includes corresponding optical or radio frequency transceivers 78a and 80a by which the projector sensor 28a communicates interaction signals through the bus 42 to the generator controller 38 and through which the projector sensor 28a receives signals from the controller 38 to control the display of the control panel image 24a. As an alternative to the wireless communication link 76a, an electrical conductor cable (not shown) can replace the wireless communication link 76a, if desired. However, such an electrical cable must be sterilized if the virtual pad 82 is to be placed in the sterile field.

Figure 9:
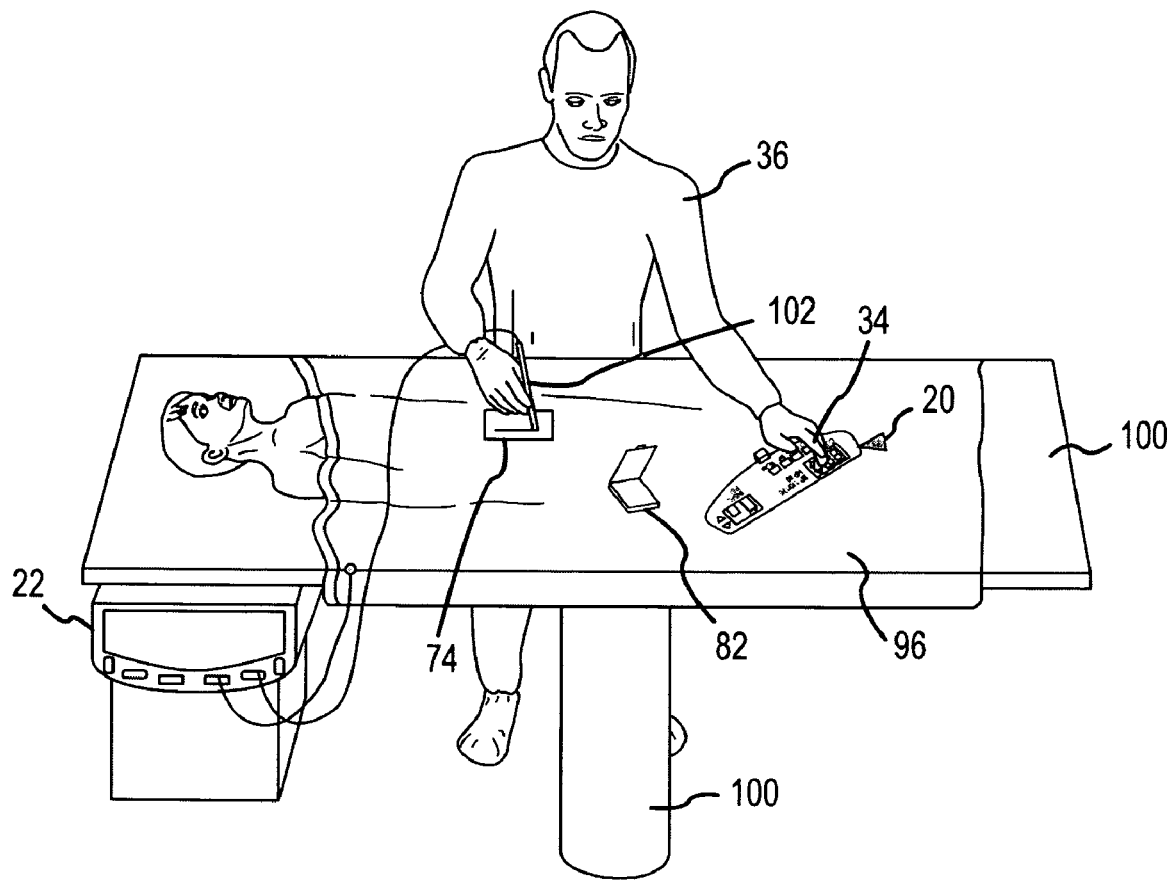
FIG. 9 is a perspective view of an operating room in which the electrosurgical generator, virtual control panel and virtual pad shown in FIGS. 1, 4, 6 and 8, are shown in use by a surgeon on a patient.

Also shown in FIGS. 7 and 9 is a detachable control panel 20 which may be used in conjunction with the virtual pad 82. Under these circumstances, the virtual pad 82 will typically be used to display information concerning the functionality of the electrosurgical generator 22. However, the contact control areas 26 and 26a, or the display areas 27 and 27a, may be divided, shifted and arranged between the display surfaces 44 and 44a as desired so as to distribute the input control and information display functionality between the virtual control panel 26 and the virtual pad 82. Prints or overlays may also be used as whole or partial substitutes for all or a portion of the control panel image 24a, in the manner previously described.

The virtual pad 82 is shown in more detail in FIG. 8. The display surface structure 30a is connected by a hinge 83 to a base piece 84. The hinge 83 permits the display surface structure 30a to be oriented at an angle to the horizontal, while the base piece 84 supports the virtual pad 82. A hood 92 is attached to an upper edge of the display surface structure 30a and curves upward, forward and away from the display surface 44a of the display surface structure 30a. The hood 92 is attached to an upper edge of the display surface structure 30a to shield the projected control panel image 24a from the operating room lights to thereby prevent the image 24a from being washed out. The hood 92 may or may not be necessary, depending on the intensity of the ambient operating room lights and the intensity of the projected image 24a.

The projector sensor 28a preferably has a detachable connection (not shown) for attaching the projector sensor 28a to, and removing the projector sensor 28a from, the display surface structure 30a. Part of the detachable connection (not shown) preferably includes power contacts or pads (not shown) on a surface of the display surface structure 30a by which to electrically connect the projector sensor 28a and transceiver 80a to a battery pack power source 94. The battery pack power source 94 is connected to or made integral with a base piece 84. The battery pack power source 94 is preferably relatively flat and gives weight to the base piece 94 to help hold the virtual pad 82 in place on the support with the display surface structure 30*a* oriented at the angle relative to a horizontal reference plane. The base piece 84 can also be detachably attached by adhesive pads 98, for example, to a support such as surgical drapes 96 (FIG. 9). The adhesive pads 98 also help to hold the virtual pad 82 in place, and prevent the display surface structure 30*a* from tipping.

The virtual pad 82 is preferably placed in the peripheral view of the surgeon 36 during surgery, such as on the surgical drapes 96 adjacent to the surgical site 74 (FIG. 9). The display surface 44*a* of the virtual pad 82 is sized to suit the surgeon's preferences and space limitations encountered at the surgical site 74. The hinge 83 between the display surface structure 30*a* and the base piece 84 holds the display surface structure 30*a* at the desired angle for viewing by the surgeon 36. In the absence of an external force, friction at the hinge 83 holds the display surface structure 30 and base piece 84 at a fixed angle. The adhesive pads 98 connected to the base piece 84 also assist in maintaining the display surface structure 30*a* at the desired viewing angle. The ability to adjust the angle of the display surface structure 30*a* (and the display surface 44*a*) and to position the virtual pad 82 at a location within the sterile field adjacent to the surgical site 74, permits the virtual pad 82 to be located and oriented as desired by the surgeon 36, irrespective of the position of the electrosurgical generator 22.

The detachable virtual control panel 20 shown in FIG. 9 may also be located on the surgical drapes 96 within the peripheral vision of the surgeon 36. Because the virtual control panel 20 is detachable, the electrosurgical generator 22 can be located under the operating table 100 where it is out of the way. By having the electrosurgical generator 22 under the operating table 100, the operating room is less congested and the cables that run from the electrosurgical generator 22 to a hand piece 102 used by the surgeon 36 to apply the electrical energy at the surgical site 74 are less likely to get in the way or to be tripped over.

The sterilized, detached virtual control panel 20 allows the surgeon 36 to control directly the functional parameters of the electrosurgical generator 22 within the sterile field. The surgeon 36 can physically interact directly with the virtual control panel 20 to increase or decrease the power delivered by the electrosurgical generator 22 (FIG. 9) by interacting with the contact control areas 26 (FIG. 4). In a similar manner, the surgeon can also directly observe the output characteristics of the electrosurgical generator, such as a display of the amount of output power delivered. Similar benefits may also be achieved by using the virtual pad 82. If desired by the surgeon, multiple virtual pads 82 can be used. Under such circumstances, each of the virtual pads 82 would preferably display different information and provide different options for control inputs.

The virtual control panel 20 can be used with a variety of electrosurgical generators 22 by changing the configuration of the projected control panel image 24 and the contact control areas of the control panel image 24. Since the virtual control panel 20 and the virtual pad 82 do not use physical components such as liquid crystal displays or push buttons (not shown), the control panel images 24 and 24*a* of the virtual control panel 20 and the virtual pad 82, respectively, can be changed to suit the requirements of the user irrespective of the particular electrosurgical generator 22. Consequently, the layout and presentation of the control panel images 24 and 24*a* are not confined by the original physical layout of physical components on a conventional control panel for an electrosurgical generator. Furthermore, the control panel images 24 and 24*a* can be made uniform and consistent for better recognition and interaction by the surgeon, regardless of the type of electrosurgical generator 22 with which the virtual control panel 20 and the virtual pad 82 may be used. Many other advantages and improvements will be apparent upon gaining a complete understanding of the significance of the present intention.

A presently preferred embodiment of the present invention and many of its improvements have been described with a degree of particularity. This description is a preferred example of implementing the invention, and is not necessarily intended to limit the scope of the invention. The scope of the invention is defined by the following claims.

What is claimed:

1. An electrosurgical generator having a virtual control panel for controlling functionality of the electrosurgical generator in response to interrogation of an object interacting with a control panel image, the virtual control panel comprising:
   a display surface structure having a display surface upon which the control panel image is located;
   a sensor connected to the display surface structure to interrogate optically contact interaction of the object with the control panel image at a location on the display surface separated from the sensor and to supply an interaction signal indicative of contact interaction of the object with the control panel image; and the electrosurgical generator comprising:
   a generator controller operative to control functionality of the electrosurgical generator, the generator controller receiving the interaction signal and controlling functionality of the electrosurgical generator in response to the interaction signal.

2. An electrosurgical generator as defined in claim 1, wherein the virtual control panel further comprises:
   a projector connected to the display surface structure to project optically the control panel image on the display surface.

3. An electrosurgical generator as defined in claim 1, wherein:
   the control panel image is printed and attached to the display surface.

4. An electrosurgical generator as defined in claim 1, wherein:
   the electrosurgical generator includes an exterior housing;
   the display surface structure is a portion of the housing; and the virtual control panel further comprises:
   a projector connected to the display surface structure to project optically the control panel image on the display surface.

5. An electrosurgical generator as defined in claim 1, wherein:
   the electrosurgical generator includes an exterior housing;
   the display surface structure is separate from the housing; and the virtual control panel further comprises:
   a projector connected to the display surface structure to project optically the control panel image on the display surface.

6. An electrosurgical generator as defined in claim 5, wherein:
   the display surface structure is attachable to and detachable from the housing.

7. An electrosurgical generator as defined in claim 6, further comprising:
   a wireless communication link operative between the virtual control panel and the electrosurgical generator to communicate the interaction signal from the virtual control panel to the generator controller.

8. An electrosurgical generator as defined in claim 7, wherein:
the wireless communication link uses radio frequency electromagnetic waves to communicate the interaction signal from the virtual control panel to the generator controller.

9. An electrosurgical generator as defined in claim 6, wherein:
the display surface structure is sterilizable.

10. An electrosurgical generator as defined in claim 9, wherein:
the display surface structure is disposable after use at a surgical site.

11. An electrosurgical generator as defined in claim 1, wherein:
the display surface structure and the sensor are sterilizable.

12. An electrosurgical generator as defined in claim 11, wherein:
the display surface structure and the sensor are disposable after use at a surgical site.

13. An electrosurgical generator as defined in claim 1, wherein the virtual control panel further comprises:
a projector connected to the display surface structure to project optically the control panel image on the display surface; and wherein:
the projector is sterilizable.

14. An electrosurgical generator as defined in claim 13, wherein:
the display surface structure and the sensor and the projector are disposable after use at a surgical site.

15. An electrosurgical generator as defined in claim 1, wherein:
the control panel image includes a contact control area and a display area, the contact control area representing control functionality of the electrosurgical generator, the display area presenting information describing functionality of the electrosurgical generator; and
the sensor interrogating contact interaction of the object only within the contact control area of the control panel image.

16. An electrosurgical generator as defined in claim 15, wherein the virtual control panel further comprises:
a projector connected to the display surface structure to project optically a contact control area and a display area of the control panel image on the display surface, the projector further projecting optically information describing functionality of the electrosurgical generator in the display area of the control panel image.

17. An electrosurgical generator as defined in claim 16, wherein:
the projector is connected to the generator controller to receive information signals supplied from the generator controller;
the generator controller supplies information signals to the projector indicative of the information describing functionality of the generator; and
the projector responds to the information signals to project the information describing functionality of the electrosurgical generator in the display area of the control panel image.

18. An electrosurgical generator as defined in claim 16, wherein:
the control panel image includes a plurality of different contact control areas each of which represents a different control function of the electrosurgical generator;
the sensor optically interrogates contact interaction of the object with each of the different contact control areas and generates the interaction signal related to the contact interaction of the object with each of the contact control areas; and
the generator controller responds to the interaction signal to control the functionality of the electrosurgical generator in accordance with the control function interrogated by contact interaction of the object with the corresponding contact control area.

19. An electrosurgical generator as defined in claim 16, wherein:
the control panel image includes a plurality of different contact control areas each of which represents a different control function of the electrosurgical generator;
the sensor interrogates contact interaction of the object with each of the different contact control areas and generates the interaction signal related to contact interaction of the object with each of the contact control areas; and
the generator controller responds to each of the different interaction signals to control functionality of the electrosurgical generator in accordance with the control function interrogated by contact interaction of the object with the corresponding contact control area.

20. An electrosurgical generator as defined in claim 1, wherein the virtual control panel further comprises:
a projector connected to the display surface structure to project optically a plurality of different contact control areas of the control panel image on the display surface, each contact control area representing a different control function of the electrosurgical generator; and wherein:
the sensor comprises a light source which scans a transmitted light beam over the contact control areas of the control panel image, and a light receptor sensor which receives a received light beam created by reflection of the transmitted light beam from the object upon contact interaction with each contact control area; and the virtual control panel further comprises:
a device controller connected to the light source and the light receptor sensor, the device controller operatively controlling the light source to scan the transmitted light beam over the contact control areas at a predetermined scanning angle at each instance of time, and the device controller operatively determining the contact interaction of the object with a contact control area based on the scanning angle and the received light beam.

21. An electrosurgical generator as defined in claim 20, wherein:
the light source delivers pulses of light as the transmitted light beam;
the received light beam is formed by pulses of light which are time shifted relative to the corresponding pulses of the transmitted light beam as a result of reflection of the transmitted light beam from the object; and
the device controller operatively determines an interaction position where the object interacts with a contact control area based on the time shift of the corresponding pulses of the transmitted and received light beams in addition to the predetermined scanning angle.

22. An electrosurgical generator as defined in claim 21, wherein:

the projector projects a projection light beam on the display surface to optically create the contact control areas;

the device controller is operatively connected to the projector to coordinate the location where the projection light beam creates each of the contact control areas relative to the interaction position where the object contacts the contact control areas of the control panel image.

23. An electrosurgical generator as defined in claim 1, further comprising:

a virtual pad in addition to the virtual control panel, the virtual pad including a pad display surface structure having a pad display surface;

a pad projector positioned relative to the pad display surface structure to project optically a pad control panel image on the pad display surface;

a pad sensor connected to the pad display surface structure to interrogate contact interaction of the object with the pad control panel image at a location on the pad display surface separated from the sensor and to supply a pad interaction signal indicative of contact interaction of the object with the pad control panel image; and wherein:

the generator controller is connected to receive the pad interaction signal and to control the functionality of the electrosurgical generator in response to the pad interaction signal in response to contact interaction of the object with the pad control image.

24. An electrosurgical generator as defined in claim 23, wherein:

the pad projector creates the pad control panel image with a pad contact control area and a pad display area, the pad contact control area representing control functionality of the electrosurgical generator, the pad display area presenting information describing functionality of the electrosurgical generator; and the pad projector projecting the information describing functionality of the electrosurgical generator in the pad display area of the pad control panel image.

25. An electrosurgical generator as defined in claim 24, wherein:

the pad projector is connected to the generator controller to receive information signals supplied by the generator controller;

the generator controller supplies information signals to the pad projector indicative of the information describing the functionality of the generator; and the pad projector responds to the information signals to project the information describing functionality of the electrosurgical generator in the pad display area of the pad control panel image.

26. An electrosurgical generator as defined in claim 25, further comprising:

a wireless communication link connecting the virtual pad and the generator controller and operative to communicate the interaction signal and the information signals between the virtual pad and the generator controller.

27. An electrosurgical generator as defined in claim 23, wherein the virtual pad further comprises:

a hood connected to the pad display surface structure and extending above the pad display surface for shielding the pad control panel image from ambient light.

28. An electrosurgical generator as defined in claim 23, wherein the virtual pad further comprises:

a base piece connected to the pad display surface structure to support the virtual pad and orient the pad display surface structure at an angle relative to a horizontal reference; and a self-contained power supply connected to one of either the base piece or the pad display surface structure for supplying power to the pad projector.

29. A virtual control panel for use with an electrosurgical generator to control functionality of an electrosurgical generator in response to interrogation of an object interacting with virtual control panel, the electrosurgical generator including a generator controller to control the functionality of the electrosurgical generator in response to control input signals, the virtual control panel comprising:

a display surface structure having a display surface;

a control panel image on the pad display surface; and a sensor connected to the display surface structure to interrogate optically contact interaction of the object with the control panel image at a location on the display surface separated from the sensor, the sensor creating an interaction signal indicative of contact interaction of the object with the control panel image, the sensor supplying the interaction signal as a control input signal to the generator controller by which to cause the generator controller to control the functionality of the electrosurgical generator in response to the contact interaction of the object with the control panel image.

30. A virtual control panel as defined in claim 29, wherein:

the control panel image is printed and attached to the display surface.

31. A virtual control panel as defined in claim 29, further comprising:

a projector connected to the display surface structure to project optically the control panel image on the display surface.

32. A virtual control panel as defined in claim 31, wherein:

the control panel image projected by the projector includes a contact control area and a display area, the contact control area representing control functionality of the electrosurgical generator, and the display area presenting information describing functionality of the electrosurgical generator;

the sensor interrogates contact interaction of the object with the contact control area of the control panel image; and the projector projecting information describing functionality of the electrosurgical generator in the display area of the control panel image in response to information signals supplied by the generator controller.

33. A virtual control panel as defined in claim 32, further comprising:

a transmitter receiver connected to the projector and sensor to communicate wirelessly the interaction and information signals to and from the generator controller.

34. A virtual control panel as defined in claim 29 which is sterilizable.

35. A virtual control panel as defined in claim 29 which is disposable after use at a surgical site.

36. A virtual control panel as defined in claim 29, further comprising:

a projector connected to the display surface structure to project optically the control panel image on the display surface.

37. A method for controlling functionality of an electrosurgical generator, comprising:

presenting a control panel image on a display surface of a display surface structure;

including within the control panel image a contact control area which represents a control function of the electrosurgical generator;

interacting an object by contact with the contact control area to select functionality to be performed by the electrosurgical generator;

optically interrogating the contact control area for contact interaction by the object at the display surface structure; and controlling the functionality of the generator in response to interrogating the contact interaction of the object with the contact control area.

38. A method as defined in claim 37, further comprising:
presenting the control panel image by optically projecting the control panel image onto the display surface.

39. A method as defined in claim 37, further comprising:
presenting the control panel image by attaching a printed representation of the control panel image to the display surface.

40. A method as defined in claim 37, further comprising:
using a finger of an operator of the electrosurgical generator as the object for interacting with the control panel image.

41. A method as defined in claim 37, further comprising:
positioning the display surface structure and the display surface within a sterile field at a surgical site.

42. A method as defined in claim 37, further comprising:
physically separating the display surface structure and the display surface from the electrosurgical generator;
positioning the display surface structure and the display surface within a sterile field at a surgical site; and
positioning the electrosurgical generator outside of the sterile field at the surgical site.

43. A method as defined in claim 37, wherein the electrosurgical generator includes an exterior housing, and the method further comprises:
using a portion of the exterior housing of the electrosurgical generator as the display surface structure; and
presenting the control panel image by optically projecting the control panel image onto the portion of the housing forming the display surface structure.

44. A method as defined in claim 37, wherein the electrosurgical generator includes an exterior housing, and the method further comprises:
separating the display surface structure from the housing.

45. A method as defined in claim 44, further comprising:
selectively attaching the display surface structure to the housing; and
selectively detaching the display surface structure from the housing.

46. A method as defined in claim 44, further comprising:
sterilizing the display surface structure prior to controlling the functionality of the electrosurgical generator during a surgical procedure.

47. A method as defined in claim 46, further comprising:
disposing of the display surface structure after controlling the functionality of the electrosurgical generator during the surgical procedure.

48. A method as defined in claim 46, further comprising:
using a sensor connected to the display surface structure to optically interrogate the contact control area for contact interaction by the object; and
sterilizing the sensor prior to controlling the functionality of the electrosurgical generator during the surgical procedure.

49. A method as defined in claim 48, further comprising:
disposing of the display surface structure and the sensor after controlling the functionality of the electrosurgical generator during the surgical procedure.

50. A method as defined in claim 48, further comprising:
using a projector connected to the display surface structure to present the control panel image by optically projecting the control panel image onto the display surface; and
sterilizing the projector prior to controlling the functionality of the electrosurgical generator during the surgical procedure.

51. A method as defined in claim 50, further comprising:
disposing of the display surface structure and the sensor and the projector after controlling the functionality of the electrosurgical generator during the surgical procedure.

52. A method as defined in claim 37, further comprising:
presenting the control panel image by optically projecting the control panel image onto the display surface;
including a contact control area and a display area in the presented control panel image;
permitting control over the functionality of the electrosurgical generator by interacting the object only by contact with the contact control area; and
presenting information describing functionality of the electrosurgical generator in the display area.

53. A method as defined in claim 52, further comprising:
supplying information signals from the generator controller to the virtual control panel which contain information describing the functionality of the generator;
supplying interaction signals to the generator controller from the virtual control panel to control the functionality of the generator; and
wirelessly communicating the interaction and information signals between the electrosurgical generator and the virtual control panel.

54. A method as defined in claim 52, further comprising:
including in the control panel image a plurality of different contact control areas each of which represents a different control function of the electrosurgical generator;
optically interrogating contact interaction of the object with each of the different contact control areas;
selecting different control functions of the electrosurgical generator by contact interaction of the object with the corresponding contact control areas.

55. A method as defined in claim 37, further comprising:
including in the control panel image a plurality of different contact control areas each of which represents a different control function of the electrosurgical generator
optically interrogating contact interaction of the object with each of the different contact control areas; and
selecting different control functions of the electrosurgical generator by contact interaction of the object with the corresponding contact control areas.

56. A method as defined in claim 37, further comprising:
presenting the control panel image by optically projecting the control panel image onto the display surface;
including in the projected control panel image a plurality of different contact control areas each of which represents a different control function of the electrosurgical generator;
optically interrogating the contact control area for contact interaction by the object by scanning a transmitted light beam over the contact control areas of the control panel image, and by receiving a received light beam created by reflection of the transmitted light beam from the object;
controlling a predetermined scanning angle of the transmitted light beam over the contact control areas at each instance of time; and
interrogating the contact interaction of the object with a contact control area based on the scanning angle and the received light beam.

57. A method as defined in claim 56, further comprising:
delivering pulses of light as the transmitted light beam;
forming the received light beam by pulses of light which are time shifted relative to the corresponding pulses of the transmitted light beam by reflection of the transmitted light beam from the object; and
determining an interaction position where the object interacts by contact with a contact control area based on the relative time shift of the corresponding pulses of the transmitted and received light beams in addition to the predetermined scanning angle.

58. A method as defined in claim 57, further comprising:
projecting a projection light beam on the display surface to optically create the contact control areas of the control panel image on the display surface; and
coordinating the location where the projection light beam creates the contact control areas relative to the interaction position where the object interacts by contact with the contact control areas of the control panel image.

59. A method as defined in claim 37, further involving the use of a virtual pad in addition to the virtual control panel, the method further comprising:
optically projecting a pad control panel image on a pad display surface of a pad display surface structure of the virtual pad;
including within the pad control panel image a pad contact control area which represents a control function of the electrosurgical generator;
interacting an object by contact with the pad contact control area as a designation of a selected control function to be performed by the electrosurgical generator;
optically interrogating the pad contact control area for contact interaction by the object; and
controlling the functionality of the generator in response to interrogating the interaction of the object by contact with the pad contact control area and in response to interrogating the interaction of the object by contact with the contact control area of the virtual control panel.

60. A method as defined in claim 37, further comprising:
shielding the control panel image from being washed out by ambient light.

* * * * *